United States Patent [19]

Deckert et al.

[11] Patent Number: 4,681,563
[45] Date of Patent: Jul. 21, 1987

[54] FLOW CONTROL SYSTEM

[75] Inventors: Clinton Deckert; Larry L. Wilson, both of Poway, Calif.

[73] Assignee: Centaur Sciences, Inc., Stamford, Conn.

[21] Appl. No.: 727,840

[22] Filed: Apr. 26, 1985

[51] Int. Cl.[4] ............................................. A61F 2/00
[52] U.S. Cl. ............................ 604/67; 128/DIG. 13; 137/487.5; 340/619
[58] Field of Search .................................. 604/65-67, 604/245; 128/DIG. 13; 340/619; 137/487.5, 486

[56] References Cited

U.S. PATENT DOCUMENTS

| | | | |
|---|---|---|---|
| 3,655,095 | 4/1972 | Kienitz | 604/65 |
| 4,094,318 | 6/1978 | Burke et al. | 128/DIG. 13 |
| 4,372,304 | 2/1983 | Avakian | 137/486 |
| 4,504,263 | 3/1985 | Steuer et al. | 604/65 |
| 4,509,943 | 4/1985 | Hanzawa | 604/67 |
| 4,570,639 | 2/1986 | Miodounik | 604/65 |

Primary Examiner—Carroll B. Dority, Jr.
Attorney, Agent, or Firm—Chilton, Alix & Van Kirk

[57] ABSTRACT

A dual controller for an IV infusion system comprises a microprocessor to concurrently control the rate of infusion through two IV units. The control of the rate of infusion is provided by a stepper motor driven regulator which is selectively positionable for compressibly engaging the IV tubing. A flow sensor employs a case of infrared transparent material which mounts to a drip chamber of the infusion unit. The flow sensor provides an output pulse to the microprocessor in response to a drop of fluid in the drip chamber interrupting a light path extending from an array of light emitting diodes and a photo transistor. The light emitting diodes are pulsed between energized and non-energized states so that changes in the ambient light level do not adversely effect the sensed drop rate.

8 Claims, 11 Drawing Figures

FLOW CONTROL SYSTEM

BACKGROUND OF THE INVENTION

(1) Field of the Invention

The present invention relates to the precise exercise of control over the gravity flow of liquid from a reservoir to a consuming unit and particularly to regulating fluid flow in the form of discrete drops in the intravenous application of the fluid to a patient. More particularly, the present invention is directed to a microcomputer based dual intravenous fluid flow control system and to a drop sensor unit employed in such system. Accordingly, the general objects of the present invention are to provide novel and improved devices of the foregoing character.

(2) Description of the Prior Art

The present invention has particular application to medical applications wherein the flow rate and/or total quantity of a liquid being gravity fed intravenously to a patient must be precisely controlled. U.S. Pat. No. 4,372,304 discloses a flow control system which employs a microprocessor based flow control. The flow control system employs a keyboard through which information may be inputted and includes a visual display of parameters which are of interest to the operator. The microprocessor provides output signals to a stepper motor which is coupled to a restrictor having a plunger. The microprocessor provides control signals to a stepper motor which through appropriate gearing causes movement of the plunger so as to increase or decrease the compression of the plastic tube of an IV set which is captured in a disposable adaptor mounted in registration with the plunger.

U.S. Pat. No. 4,094,318 discloses an electronic control apparatus for controlling the administration of a plurality of separate fluids independently and consecutively. The electronic control apparatus includes electrical circuitry which is connected with a plurality of valve operators to operate magnetically operated valves in a plurality of sets to control flow therethrough.

BRIEF SUMMARY OF THE INVENTION

The present invention is a new and improved flow control system which employs new and improved means for sensing the flow rate or drop rate of the fluid to be administered and provides new and improved means for concurrently operating two flow controllers.

Briefly stated the invention in a preferred form is a flow sensor for detecting the drop rate in an associated drip chamber of an infusion system. The flow sensor comprises an array of infrared light emitting diodes which generate an infrared light path. A photo sensor is interposed in the light path to detect the level of light therein and to continuously generate a first signal indicative of the detected light level. A pulser periodically energizes the light emitting diodes to produce a series of energized and non-energized states. The difference between the first signal when the diodes are energized and the first signal when the diodes are not energized is electronically determined and a second signal is generated. Electronic means detect a pre-established deviation of the second signal from a reference level and produce a third signal indicative of the deviation. An output pulse is produced in accordance with the third signal. The photo transistor and the light emitting diodes are enclosed within a case which is formed of an infrared transparent material and is configured so that the light path from the diodes traverses spaced portions of the case.

In accordance with the invention, a flow control system for concurrently controlling the flow of fluid in two infusion units comprises a keyboard which inputs command and data signals indicative of a desired flow rate and fluid quantity for each of two infusion units. A pair of flow sensors are each adapted for mounting with an associated drip chamber of an infusion unit to generate a pulse corresponding to the occurrence of a falling drop in the chamber by sensing the interruption of a light path by the falling drop. A pair of controllers each of which is associated with an infusion unit variably controls the flow of fluid passing through each of the units by application of a variable compressive force. Each of the controllers is driven by a stepper motor. Microprocessor circuitry responsive to the input and data signals from the flow sensor pulses compares actual and desired fluid flow rates and generates signals for controlling the stepper motors for concurrently independently regulating the fluid flow of each of the infusion units. The processor circuitry is also programmable to activate an alarm in the event that the actual flow rate deviates from the desired flow rate for a pre-established time interval for at least one of the infusion units and to generate a signal to a motor for activating the associated controller to inhibit the flow of fluid in the infusion unit.

DETAILED DESCRIPTION OF THE INVENTION

Figure 1:
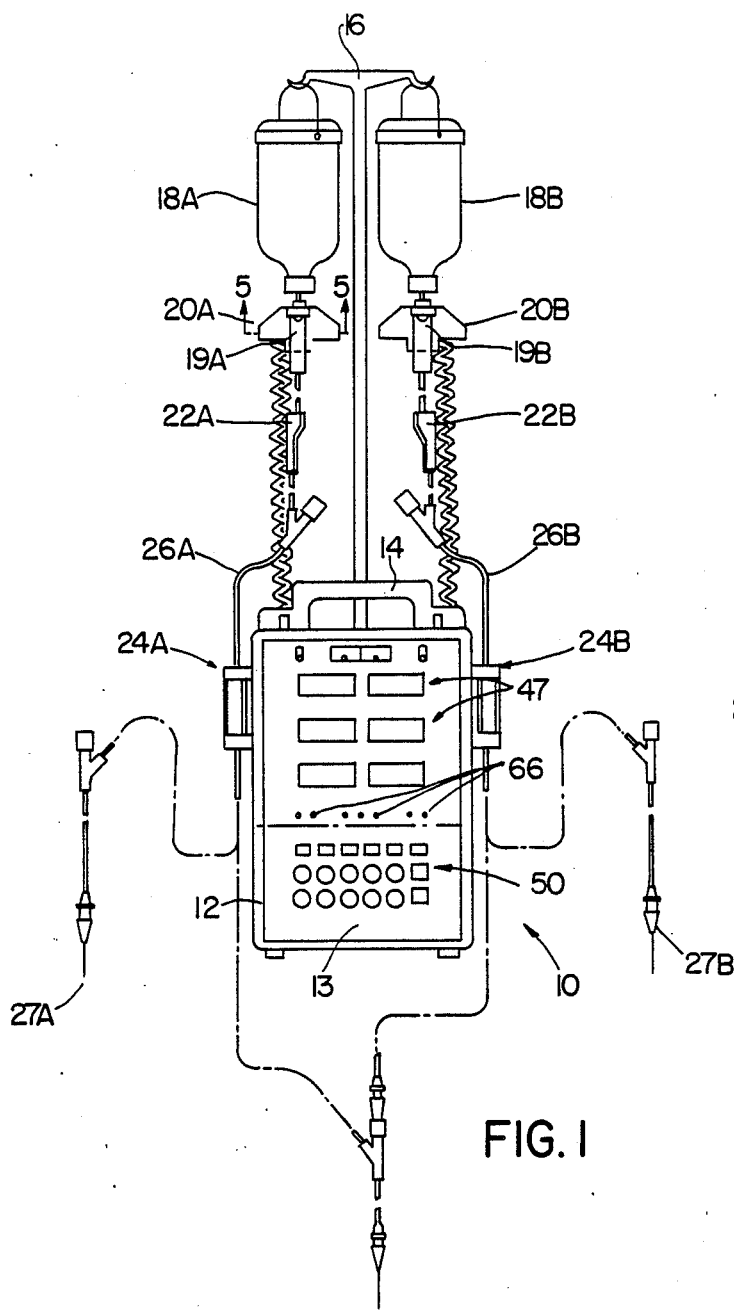
FIG. 1 is a front perspective view of a microcomputer driven dual IV system in accordance with the present invention.

With reference to the drawing wherein like numerals represent like parts throughout the several FIGURES, a portable IV controller unit in accordance with the present invention is generally designated by the numeral 10. IV controller unit 10 provides a dual channel (respectively designated by the letters A and B) rate and volume control of intravenous fluid for fluid administrations wherein gravity provides the injection pressure. IV controller unit 10 includes a substantially rectangular housing 12. Housing 12 includes a front panel 13 having controls to input a desired infusion rate, time and volume for each channel and to input whether one channel, two concurrent channels or two channels in sequence are to be employed. Various displays and indicators are also located at the front panel.

An integral carrying handle 14 extends from the upper portion of housing 12. The housing may be mounted to an IV stand 16 by means of a pole clamp (not illustrated) connecting at the rear panel of the housing. The controller unit 10 is adapted for controlling the infusion rate and volume of fluid from two separate fluid containers 18A and 18B having associated drip chambers 19A and 19B, respectively, of conventional form. Two substantially identical flow sensors 20A and 20B are clamped to the respective drip chambers of each of the corresponding IV fluid containers. Each drop of the fluid which falls into the drip chambers produces a corresponding electrical pulse which is transmitted by a corresponding cable 22A or 22B to the processing circuitry within housing 12. The rates at which the drops of fluid are actually produced as sensed by flow sensor 20A or 20B is compared within the controller circuitry with the corresponding rates selected by the operator.

Figure 8:
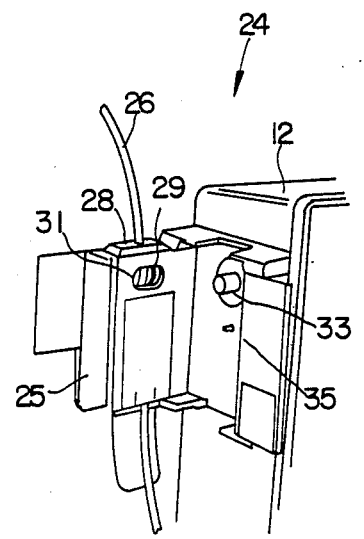
FIG. 8 is a fragmentary side perspective view of the system of FIG. 1 illustrating a regulator mounting door thereof in the open position.

Controller assemblies 24A and 24B corresponding to each of the separate fluid administration units are located at opposite sides of the housing. With reference to FIG. 8, a door 25 swings away from the housing to facilitate reception of a disposable section 26 of plastic tubing which is interposed in the IV tubing line extending from the drip chamber to the venipuncture needle 27. Tubing section 26 centrally mounts a locator case 28 forming a flow regulator opening 29. Case 28 is exteriorly dimensioned for self-aligning reception in a mounting channel of door 25 so that opening 29 aligns with a corresponding window 31 formed in door 25. An axially displaceable regulator shaft 33 is projectable through window 31 and opening 29 to provide a variable clamping engagement with the captured tubing section when the door is closed against the housing, as illustrated in FIG. 1. The regulator shaft is driven by a stepper motor which is controlled by processor circuitry as described hereinafter. The IV tubing is positioned relative to the end of the shaft 33 so that clamp pressure applied by the shaft against the tubing results in the achievement of the selected rate of fluid flow through the tubing. The controller unit provides for independent and cooperative control of controller assemblies 24A and 24B. In accordance with the invention each of the channels may be used sequentially producing an alarm when the infusion is complete or the tube channels may be used concurrently or in a piggyback mode.

Additional specific details of each controller assembly 24 may be substantially identical to the corresponding control assembly disclosed in U.S. Pat. No. 4,372,304, relevant portions of which are incorporated herein by reference. The foregoing controller unit employs a microprocessor which generates signals for transmittal to a stepper motor control. The stepper motor control provides output signals for controlling the position of an output shaft of the stepper motor which drives a plunger or regulator shaft for variably compressing a flexible tube. An open door alarm switch 35 electrically communicates with the processor circuitry for signalling that the door is open.

With reference to FIG. 2, 7a, 7b and 7c the controller processing circuitry comprises a microprocessor 30, a read-only memory (ROM) 32, two random access memory - input/output devices (RAM) 34 and 36 and an address data bus 38. The lower 8 of 16 lines of the address data bus 38 are multiplexed within microprocessor 30. The foregoing lines are uni-directional in the address state and bi-directional in the data state. During the data read or write operation, the remaining address lines are active while the address/data lines are in the data mode during the first part of the address cycle. The states of the address/data lines are latched to the input of the ROM 32 through an address latch enable ALE 40. Data is then read when the microprocessor 30 first sets address bits A8 through A 13 low and RD low to place the output of ROM 32 on the data bus 38.

RAMs 34 and 36 have internal address latches and use only the 8 low order address bits. The address on these latter lines is latched internally on the falling edge of the address latch enable. The flow sensors 20A and 20B and RAMs 34 and 36 provide interrupt inputs to microprocessor 30. The inputs from the flow sensors 20A and 20B are used to sense each drop of the infusion fluid as will be further described below. A timer in RAM 36 is clocked by a 3 MHz output of microprocessor 30 to provide an interrupt signal every five milliseconds. The interrupt signal causes the microprocessor 30 to perform operations related to the real time controller functions. An interrupt signal from RAM 34 occurs each half-second and is generated by an internal timer driven by a back-up oscillator 42. The microprocessor 30 counts the number of five-millisecond interrupt signals occurring between each half-second interrupt signal to compare the clocking accuracy of the two corresponding crystals. If the number of five-millisecond interrupts in one half-second is less than 99 or more than 101, a malfunction in one of the crystal circuits is indicated, controller operation is terminated and a corresponding alarm is generated.

The RAMs 34 and 36 additionally provide data storage for microprocessor 30 and through their latchable inputs and outputs serve as interface devices between the central processing unit and the other electronic components of controller unit 10. The data which controls the RAM outputs are transmitted from microprocessor 30 over the address data bus 38 and latch to the RAM outputs. The corresponding inputs and outputs to and from each of the RAMs are indicated by the direction of the arrows in the diagram of FIG. 2.

The microprocessor 30 interrogates RAM 36 every five milliseconds to determine the state of the inputs to RAM 36. The microprocessor performs an appropriate routine in response to any one of the following operation conditions:

(1) The flow sensor 20A is or is not electrically connected with the processor circuitry;

(2) The flow controller door 25A is open;

(3) The controller unit is operated on A/C at power up conditions.

The conditions at the input of RAM 34 that produce a corresponding response are:

(1) The flow sensor 20B is nor is not electrically connected with the processor circuitry;

(2) The flow controller door 25B is open.

In the event that there is an input from the flow sensors 20A and/or 20B, the microprocessor 30 calculates the sensed drop rate and compares it to the desired calculated rate. If a flow controller door 25A or 25B is open the microprocessor generates a signal for activing an appropriate alarm.

RAM 36 strobes the six keyboard columns of keyboard 50 at five millisecond intervals. In the event that any key is closed, one of three lines from the keyboard 30 to RAM 36 will be set low. The combination of the active strobe and the active return line identify the depressed key pad. The data for the display driver is in serial form at one of the RAM 36 outputs so that data is clocked into the decoder/driver 46 which is selected through the multiplexer 48 for transmittal to the visual displays 47.

RAM 36 has direct outputs to the audible alarm device (not illustrated), the power supply 44 and the display driver/decoder 46. RAM 34 has direct outputs to the various panel indicators and to the two stepper motors 52A and 52B associated with the respective controller assemblies 24A and 24B The power switch contacts are by-passed when the power is turned off. When the on/off switch 58 contacts have been opened, a PWR SW signal is activated in response to a SWREQ signal when the unit is turned off. The central processing unit maintains the power which causes a by-pass circuit to remain on. The microprocessor 30 then generates a signal to the stepper motors 52A and 52B to clamp off all fluid flow through the flow controllers. If not previously accomplished, the power is deactivated after a period of one hour which de-activation removes power from the controller circuits.

Power for the controller unit 10 is provided by an internal 12-volt battery 54 or by a 12-volt AC provided by an internal transformer 56. When only the battery 54 is providing power to the unit, the display and keyboard backlighting is turned on for a twelve second period by pressing a push button (not illustrated) at the back of the controller housing. If keys are pressed while the backlighting is turned on, the backlighting remains on for twelve seconds after the last key closure. The CPU unit receives a LOW BAT input signal through RAM 36 to activate an alarm if the battery voltage falls below a predetermined level. The twelve volt power supply is employed to power the stepper motors as well as the other circuitry.

Microprocessor 30 is preferably a type 8085AH microprocessor having an internal oscillator which operates at 6 MHz and is internally divided to produce a 3 MHz clock output for clocking the internal circuits. A CLK output is also employed for clocking the RAM 36. On application of power to the controller central processor unit, the microprocessor 30 is re-set by C6 momentarily pulling RES low.

There are five interrupt inputs to microprocessor 30, e.g., INTR, TRAP, RST 7.5, RST 6.5 and RST 5.5. The INTR input is grounded. The TRAP input is the highest priority interrupt and is not maskable. Microprocessor 30 receives a TRAP input from RAM 34 every five milliseconds. The RST 7.5 input is maskable and has the next highest priority. The RST 7.5 input is received from RAM 34 every 500 milliseconds. The RST 6.5 input has the next interrupt priority and is also maskable. The RST 6.5 input is set low with each drop sensed by flow sensor 20B. The RST 5.5 input is also maskable and has the lowest interrupt priority. The RST 5.5 input is set low with each drop sensed by flow sensor 20A. The TRAP interrupt input produces an immediate response from microprocessor 30 which then executes the appropriate real time program routine. An input to one of the other interrupts if not masked and if not pre-empted by an input of a higher priority also produces an immediate response by the microprocessor 30 in the form of an execution of an appropriate program routine. Each of the foregoing interrupt inputs if not masked will be serviced in turn by microprocessor 30.

The address outputs for microprocessor 30 are AO through A15. AO through A7 are multiplexed as address/data bus lines. The read only memory (ROM) data of ROM 32 resides in the lower 8K of memory. An address for ROM 32 is applied in two steps. The first step latches the lower eight address bits AO through A7 to the lower eight address inputs of RAM 34 through address latch 40 on the falling edge of the ALE 40. Since RD is high at this time period, the data outputs of ROM 32 are in the high impedance state and data is not placed on the lines to the address/data bus 38. The second step occurs when the address/data bits of the microprocessor are multiplexed to the data input condition. Address bits A8 through A13 and RD are then applied to the remaining address inputs of ROM 32 completing the address cycle. The address data in ROM 32 is then placed on the data bus 38 and read by microprocessor 30.

RAM 34 and RAM 36 are preferably type 8155 random access memories with 256 addresses and 8 bit addressable input/output ports. The RAMs provide temporary storage of the data generated and employed by the central processor unit comprising the microprocessor 30, ROM 32, and RAMS 34 and 36. The RAMS 34 and 36 also serve as interface components between the central processing unit and the other devices of the controller unit 10. RAMS 34 and 36 are reset on power up by an RES output from LCD decoder/driver 46. The input/output ports for the RAMS are selected with the I/O M signal from LCD decoder/driver 46. RAM 34 is enabled by address line A15 and RAM 36 is enabled by address line A14.

The address bits AO through A7 are latched internally on the falling edge of ALE 40. If I/O M is low, the memory is addressed. If I/O M is in the high state, the input/output ports of RAMS 34 and 36 are addressed. RAMS 34 and 36 also contain timers. The timer in RAM 36 is triggered by the CLK signal from microprocessor 30. The timer generates a CLO signal at pin 6 to provide a TRAP interrupt to the microprocessor every five milliseconds. Back-up oscillator 42 consisting of a pair of inverters and associated components produces an interrupt output RST 7.5 at the CLO output of RAM 34 every one-half second. The central processing unit checks that 100 interrupt signals are produced by RAM 36 for each interrupt from RAM 34. In the event there is more than a five millisecond variance, the controller units are shut-down after the stepper motors 52A and 52B have clamped the administration set tubing in a no-delivery configuration and suitable alarms are actuated.

The central processing unit controls the stepper motor controls through RAM 34. In preferred form, each stepper motor 52A and 52B makes approximately 1.75 turns equivalent to 0.022 inch displacement for regulator shaft 33 from the position wherein the IV tubing is clamped to prevent all fluid flow to the position wherein the tubing is completely opened. On a power up condition of the central processing unit, the CPU unit transmits sufficient pulses to the flow controller motors 52A and 52B to turn the motors to a reference stop position to clamp off fluid flow through the IV tubing. Subsequently, the CPU keeps track of the motor position by incrementing a 2-byte counter in RAM 34 for each motor pulse in one direction and de-incrementing the counter for each motor pulse in the opposite direction. The number stored in RAM 34 is a direct indication of the motor position and hence the degree of clamping engagement relative to the administration set tubing and the rate of fluid flow therethrough. In a preferred embodiment of the invention, the flow rate is controllably variable from 5 ml/hr to 299 ml/hr in increments of 1 ml/hr.

The outputs from RAM 36 are latched and remain in the latched state until changed by the CPU. The CPU interrogates the inputs to RAM 36 every five milliseconds to determine the states of the inputs. The CPU responds with appropriate routines in response to the interrogation of the inputs. Lines PB0 through PB3 connect with multiplexer 48 for generating twelve strobes. Six of the strobes are for the keyboard 50 and six are for the display driver 46. Line PB4 is an output to the power supply 44. Line PB4 is set high when the controller unit is turned on thereby causing a transistor in the power supply to conduct and by-pass the power switch contacts. When the controller unit is turned off and the CPU has caused the stepper motors 52A and 52B to clamp the IV tubing 28 closed to the passage of fluid and a one-hour interval has elapsed, line PB4 goes low turning off the by-pass transistor and removing power from the controller unit. Line PA3 is set high when the power switch is closed and goes low when the power switch is open. The SWREQ signal signals the CPU to cause the stepper motors to clamp the IV tubing to a closed configuration before the SWREQ signal sets POWER high to turn off Q3 in the power supply thereby removing power from the main circuitry.

Line PA4 is a door condition input responsive to door alarm switch 35 of the controller assembly 24A. If the door is open, the door switch contacts are open to, through J3 to J5 and U14 to 6, set the line low. If the contacts of alarm switch 35 are closed, an alarm is created by the CPU to prevent commencement of the infusion until the door is closed. Line PA5 is the DRPSA input from flow sensor 20A. J2 through J4 is set high when the flow sensor 20A is not electrically connected and is inverted to set PA5 low.

Line PA6 connects with the power supply 44. Line PA6 is in a low state when the unit is powered from battery 54 and in a high state when powered from the alternating current via transformer 56. Line PA6 signals the CPU as to which power source is in use. Line PA7 is the LOBATT input from the power supply 44. Line PA7 goes low when the battery voltage falls to approximately 11.6 volts. A corresponding alarm response is also generated by the CPU in the event of a low battery voltage. Lines PC0 and PC1 connect for transmitting display data to the display elected by the multiplexer 48. Line PC3 provides an audible alarm output which is alternately set high then low at one-half second intervals when an alarm condition occurs. Line PC3 is also set high whenever a key is pressed or when another condition requires the audible alarm to sound. Line PC4 is a display light output to the power supply 44. The line is set high when the display light switch (not illustrated) on the back of the unit has been activated or when the unit is operating from the AC power source.

Lines PA0 through PA8 of RAM 34 are individually set high at pre-determined times to turn on various indicators of the alarm/status LED indicator 66. Lines PB0 through PB4 of RAM 34 are set high in the sequence wherein the stepper motor 52A is being activated in the desired direction. Lines PB5 through PB7 are set high in the operational sequence wherein the stepper motor 52B is being operated in the desired direction. Line PC0 forms a door condition input responsive to door alarm switch 35 of the controller assembly 24B. If the door of the controller assembly 24B is open, the door switch contacts are open and the line PC0 will be low. If the switch contacts are closed, an alarm condition is generated from the CPU and infusion is inhibited until the door is closed. Line PC1 is the DRPSB input from flow sensor 20B. J2 through J9 is set high when the flow sensor 20B is not electrically connected and is inverted to set PC1 low. Line PC2 is the LV2 input from the power supply 64 which goes low when the battery voltage falls to 10.8 volts. The CPU responds to a low power supply by closing off fluid flow through the infusion tubing at both controller assemblies and activating audible and visual alarms. Line PC3 is the LIGHTS switch input which is set low when the LIGHTS switch is closed.

Figure 5:
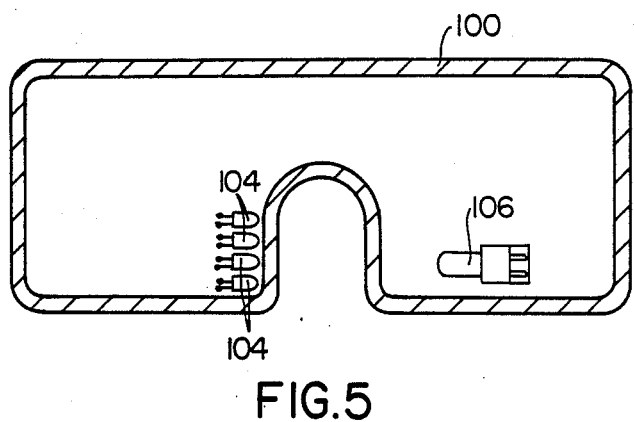
FIG. 5 is a sectional view of a flow sensor unit employed in the system of FIG. 1 taken along the line 5—5.
Figure 2:
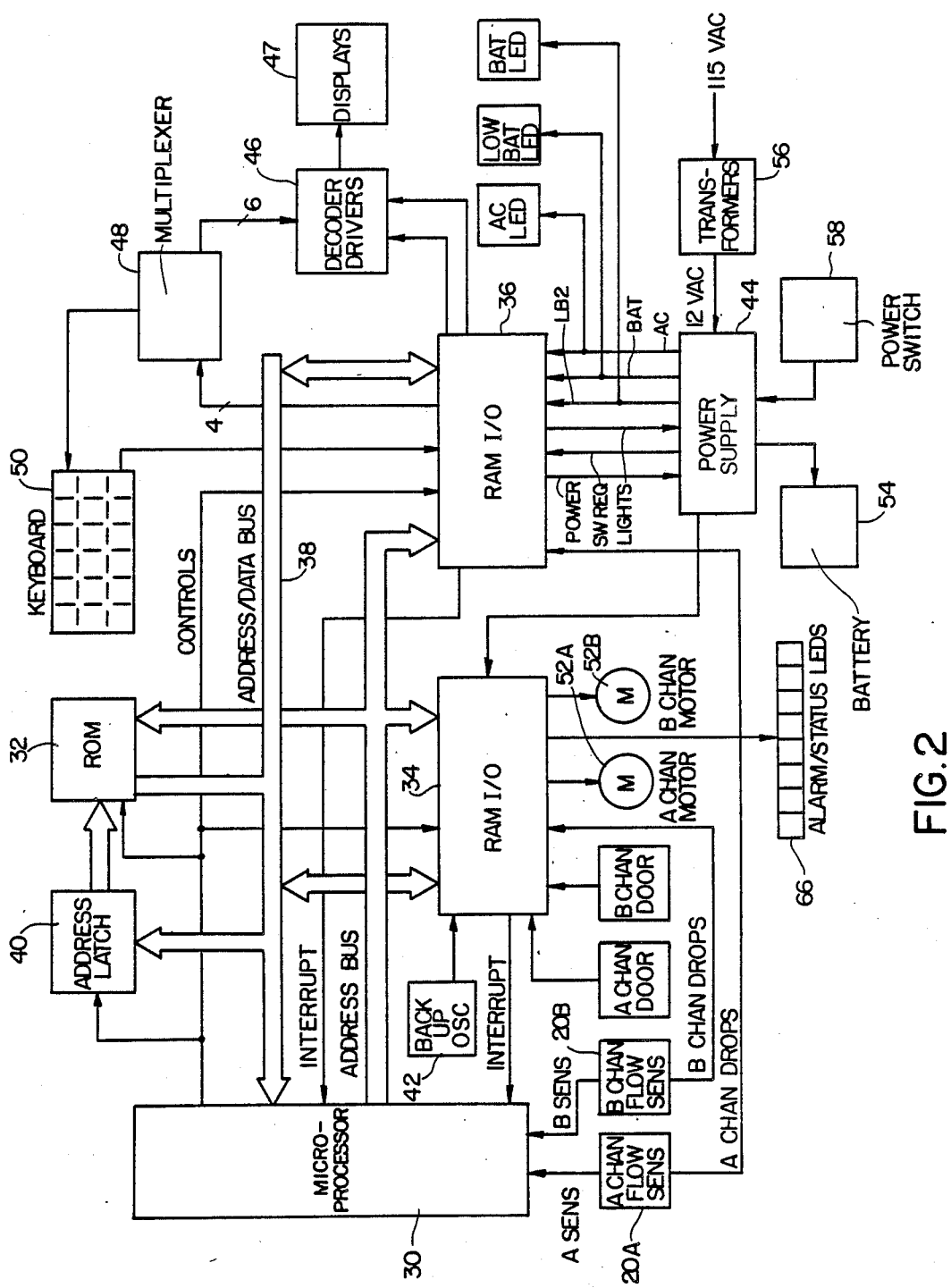
FIG. 2 is a block diagram illustrating the electrical components of the system of FIG. 1.
Figure 6A:
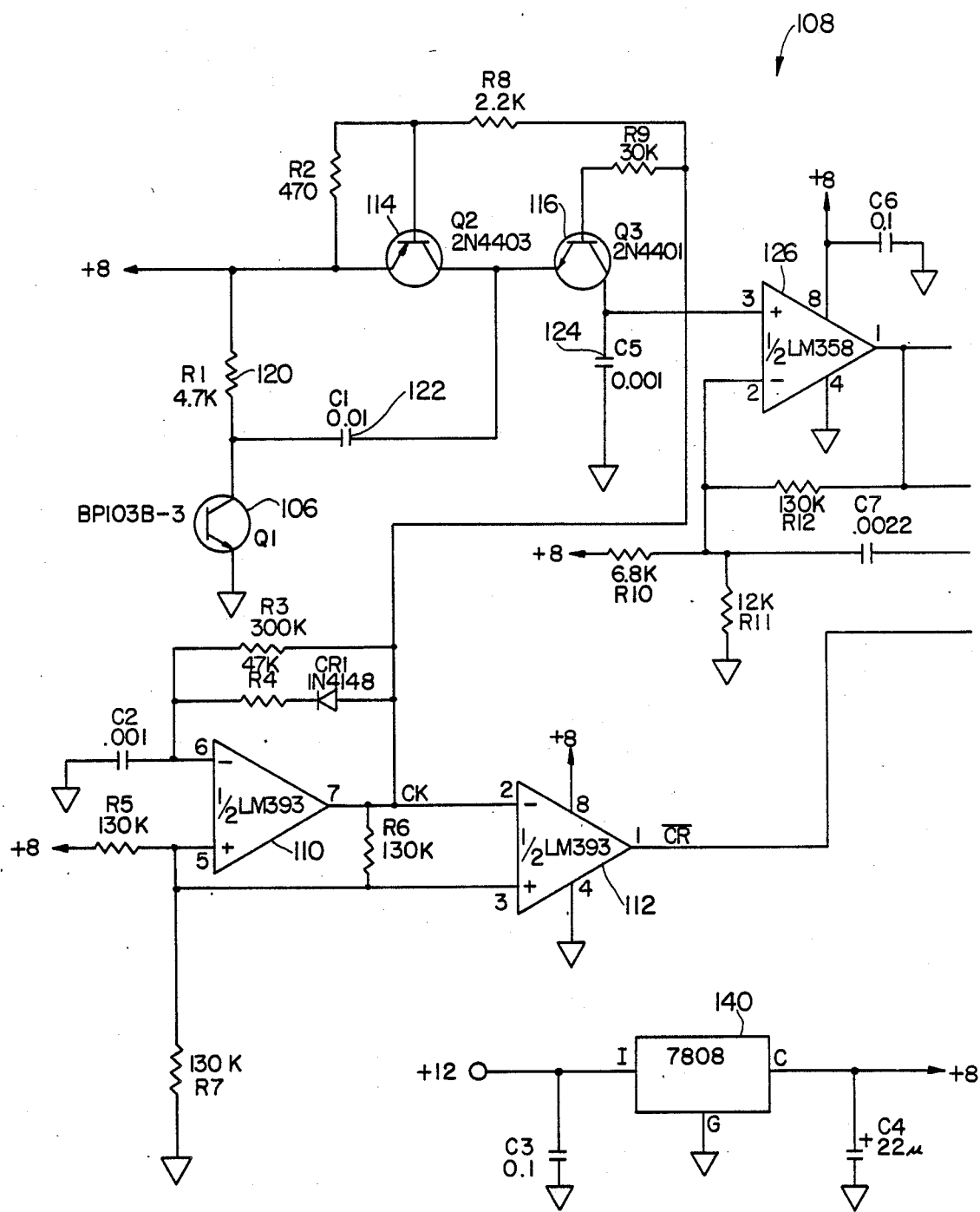
FIG. 6a and 6b together illustrate a circuit diagram for the flow sensor unit of FIG. 5.
Figure 6B:
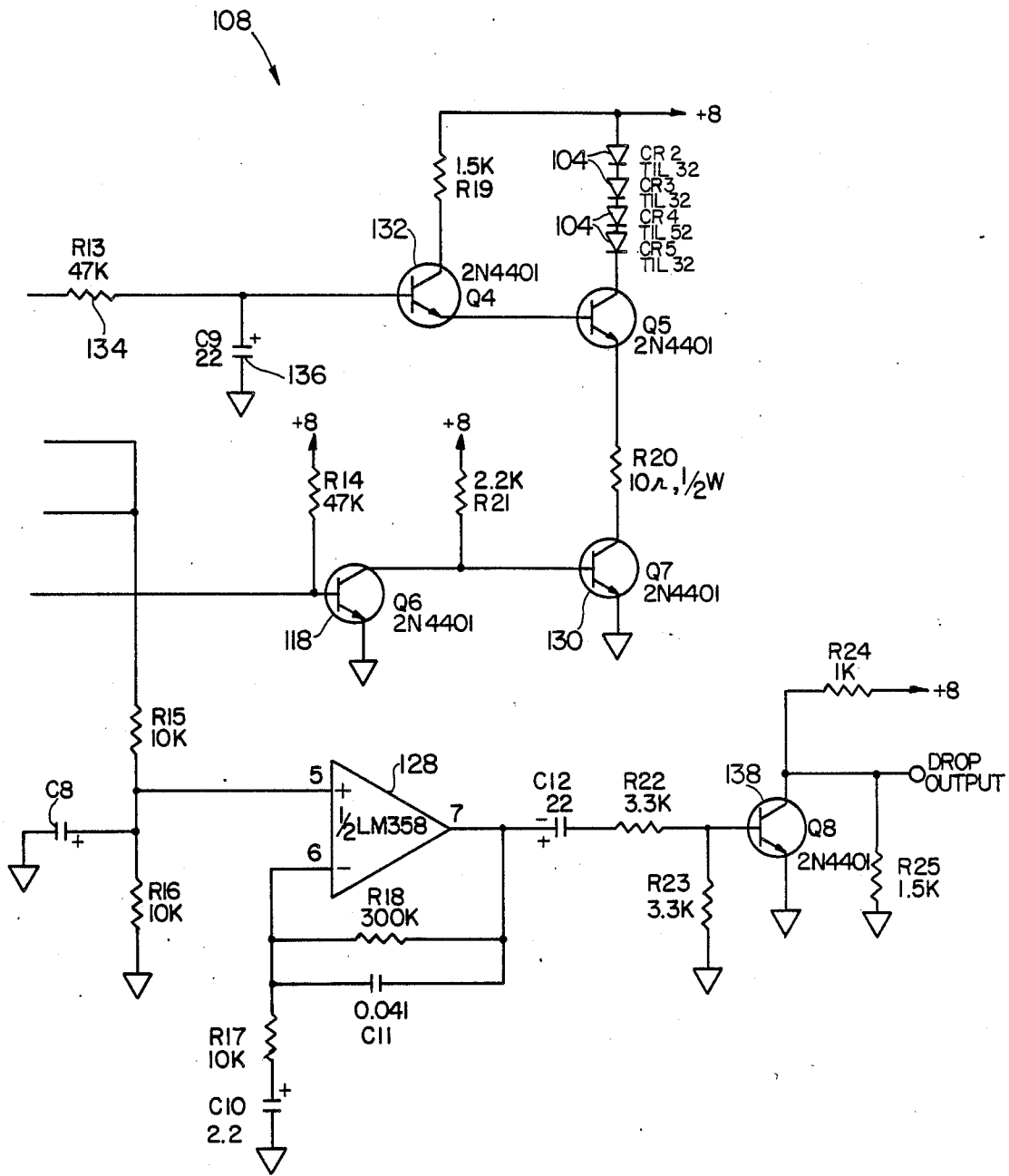
Figure 7A:
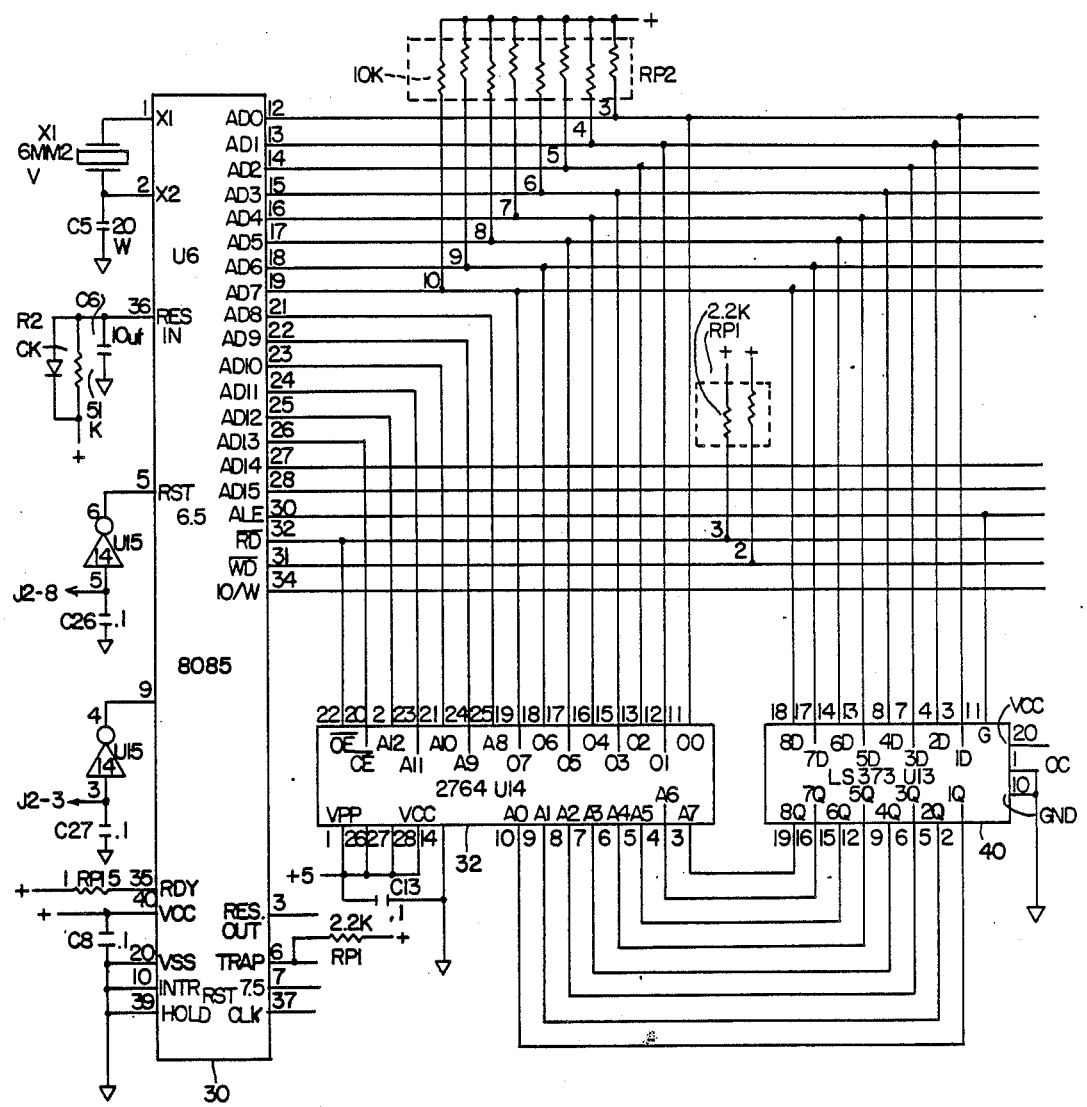
FIG. 7a, 7b, and 7c together illustrate a schematic diagram for the processor circuitry of the system of FIG. 1.
Figure 7B:
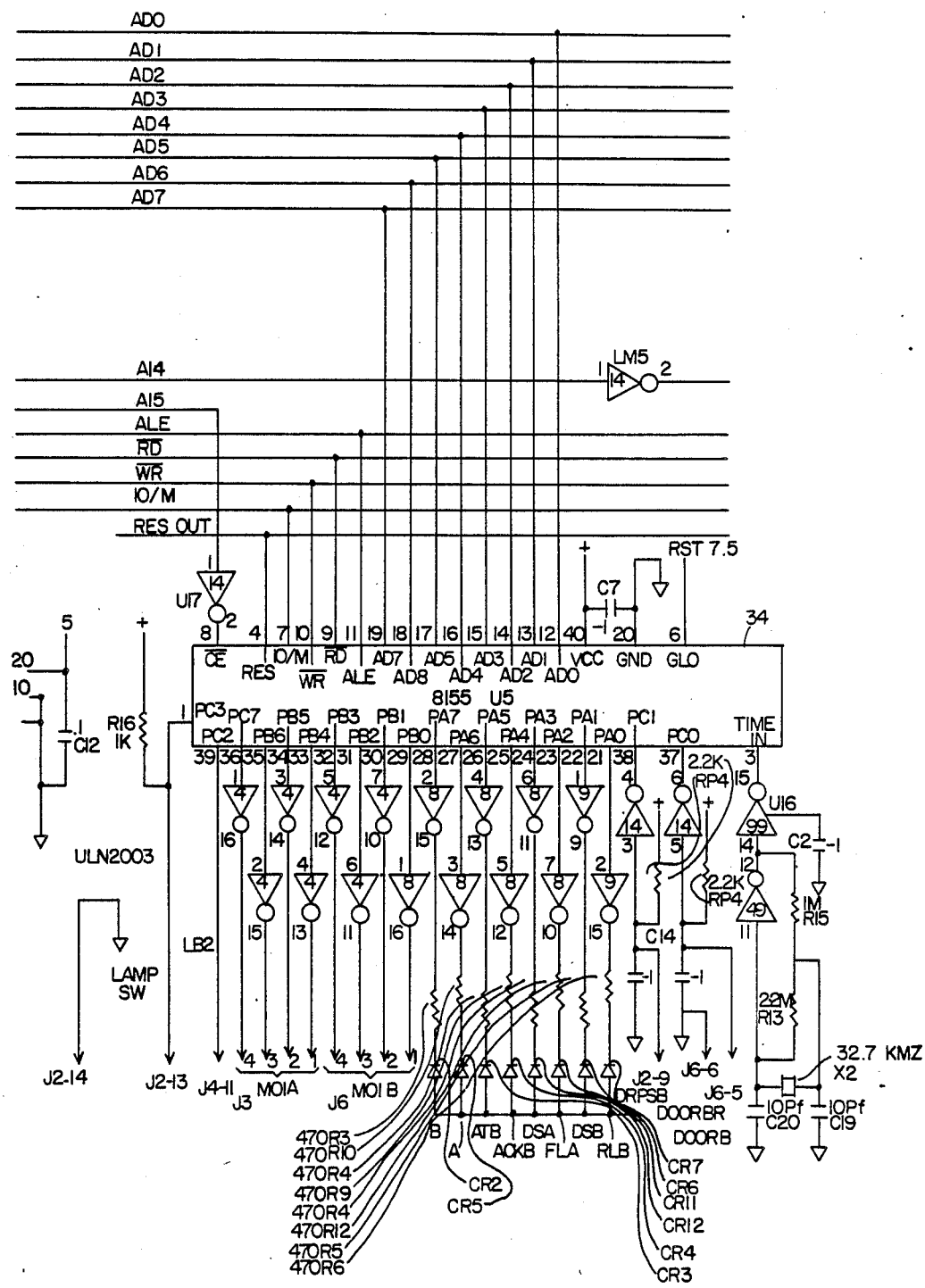
Figure 7C:
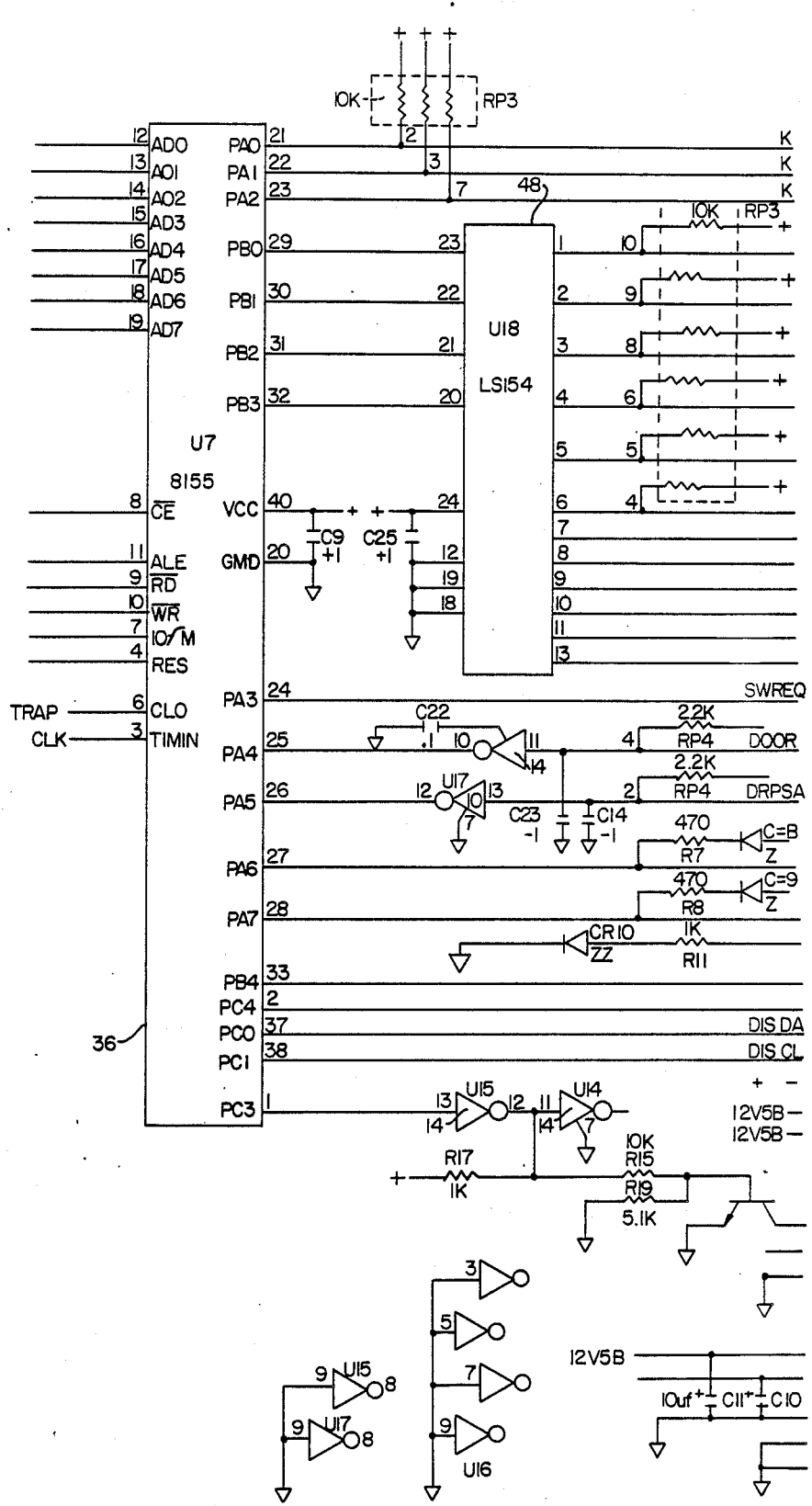

In accordance with the invention, each of the substantially identical flow sensors 20A and 20B is enclosed within a transparent case 100 which is contoured to have a quazicylindrical channel for closely accommodating the drip chamber 19A or 19B. Case 100 is formed from an infrared transparent material which absorbs nearly all of the light in the visible spectrum while transmitting a high proportion of the light in the near infrared region. A suitable material for case 100 is the MERLON9866 green plastic material marketed by Mobay Chemical Corporation. With reference to FIGS. 5, 6a, and 6b, an array of four infrared LEDs 104 and a photo transistor 106 are disposed generally diametrically relative to drip chamber 19A or 19B. Each drop falling in the drip chamber traverses the infrared light path between LEDs 104 and photo transistor 106 to interrupt the light transmission so that the photo transistor output provides a signal corresponding to each of the generated drops. The use of the foregoing described infrared transparent material for case 100 allows for the drop sensing without requiring separate lenses in the case structure. As illustrated in the drawing, the light path between LEDs 104 and photo transistor 106 essentially traverses two spaced portions of the flow sensor case 100.

With further reference to the schematic circuit diagram of FIGS. 6a and 6b flow sensor 20A generates an output pulse (DRPSA) for each drop that occurs in the associated drop chamber 19A. It should be appreciated that flow sensor 20A and flow sensor 20B are substantially identical. However, the DRPSA output from flow sensor 20A connects via line PA5 to RAM 36 while the DRPSB output from flow sensor 20B connects via line PC1 to RAM 34. The flow sensor circuit designated generally by the numeral 108 employs a closed loop system which automatically adjusts for the ambient light level as will be described below. Flow sensor circuit 108 is entirely enclosed within flow sensor case 100 with the output being transmitted via cables 22A and 22B to the controller CPU30.

A voltage comparator 110 generates a 3 KHz square wave having a ratio of approximately 9 to 1 between the high and low periods of the wave. The CK signal developed at the output of comparator 110 is inverted to CK' at the output of a second voltage comparator 112. The CK signal is applied to the bases of transistors 114 and 116. The CK' signal is applied to the base of transistor 118. The infrared LEDs 104 are turned on by the CK' signal. The CK' signal is high only ten percent of the time thereby conserving battery power and minimizing the averge LED current.

When the CK signal is low, the LEDs 104 are turned off due to the CK' being in a high state. Thus, the current through photo transistor 106 and consequently the voltage drop across resistor 120 is proportional to the ambient light level. Transistor 114 is turned on to charge capacitor 122 to the voltage drop across resistor 120. When the CK signal goes to a high state, transistor 114 is turned off and transistor 116 is turned on. Transistor 116 and capacitor 124 provide a sample and hold input for the non-inverting input of dual amplifier 126. In the absence of light from LEDs 104, the voltage at the input of amplifier 126 is 8 volts due to the algebraic sum of the voltage drop across resistor 120 and the charge on capacitor 122. Thus thereby cancelling the effects of the ambient light. The LEDs, however, are turned off by CK' being in a low state so that transistor 118 is turned off and transistor 130 is turned on.

The actual level produced across capacitor 124 is inversely proportional to the difference in the collector current of photo transistor 106 between the time that the CK signal is low (LED 104 being off) and when the CK signal is high (LED 104 being on). This latter relationship applies regardless of the level of ambient light. The difference is proportional to the light level produced by LEDs 104.

The reference level at the inverting input of amplifier 126 is approximately 5.1 volts. The output of the amplifier is proportional to the level at its non-inverting input with respect to the reference level. As the current through photo transistor 106 increases due to an increase in the infrared output from LEDs 104, a corresponding decrease in the charge on capacitor 124 and the output of amplifier 126 results. Amplifier 126 drives transistor 132 through a low pass filter comprising resistor 134 and capacitor 136. The filter filters out the 3 KHz component as well as any other changes due to a momentary decrease in detected light resulting from a traversal of a drop in the drop chamber. Transistor 132 controls the current to LEDs 104. Thus, the light level output from the infrared LEDs 104 corresponds to the current from transistor 132. The net effect of the foregoing circuit is to maintain the light output of the LEDs so that uniform level changes are produced at the input of amplifier 126 as the drops traversing the drop chamber interrupt the light path between LEDs 104 and photo transistor 106.

The output of amplifier 126 which is applied to the non-inverting input of amplifier 128 is scaled and filtered to remove any trace of the 3 KHz clock. The output of amplifier 112 is AC coupled to the base of transistor 138. The output of transistor 138 is at +5 volts in the absence of a drop interrupting the light path and is at 0 in the presence of a drop. The pulse which is produced by the presence of a drop interrupting the light path has a duration approximately equal to the time interval during which the drop passes the detection field of the photo transistor. The DRPS pulse is applied to the controller circuitry as previously described. The circuits of flow sensor 20A are powered by 8 volts obtained at the output of voltage regulator 140. The 12 volt input to voltage regulator 140 is supplied from power supply 44.

Figure 3:
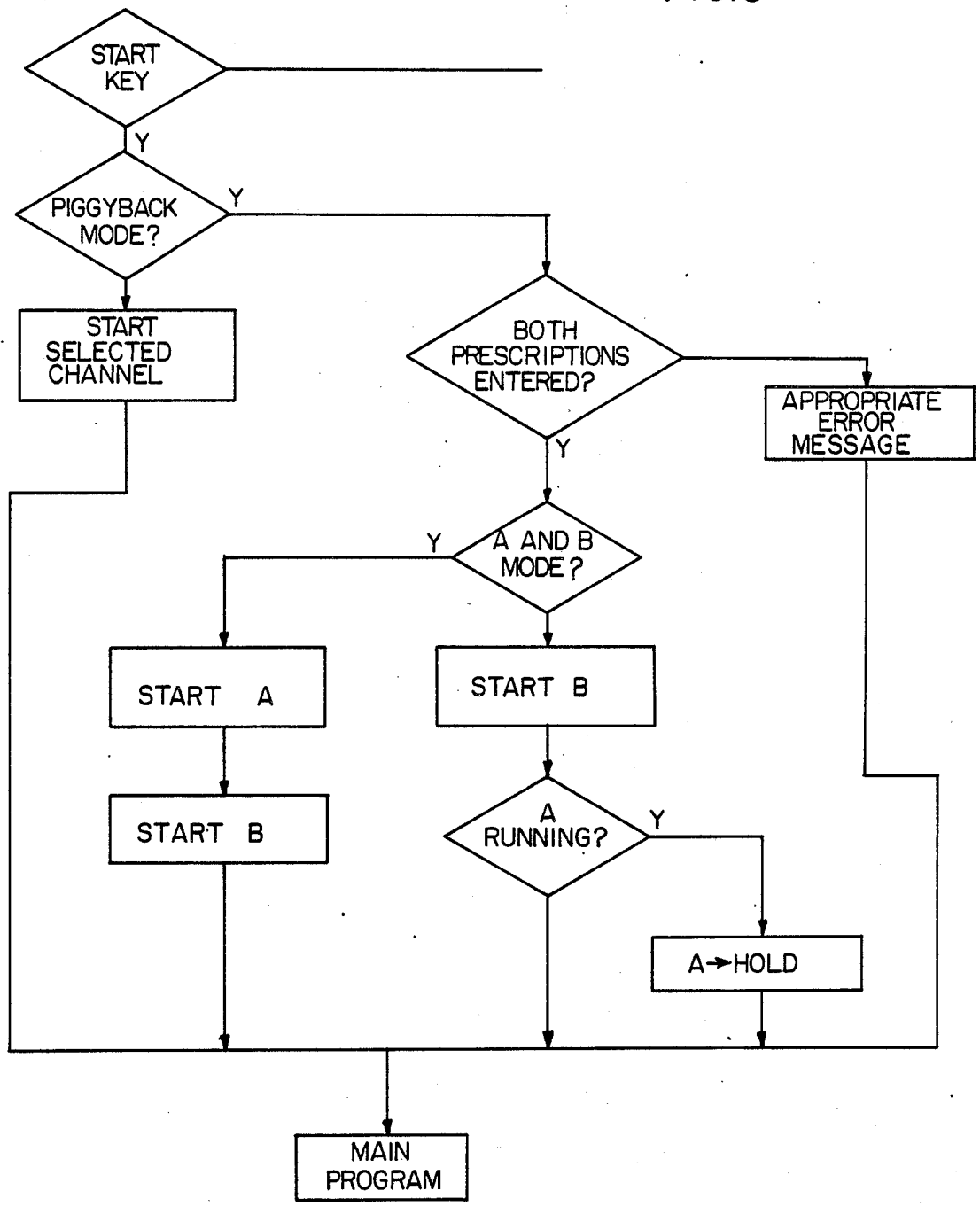
FIG. 3 is a logic diagram illustrating the operation of the system of FIG. 1 for the start phase of operation.
Figure 4:
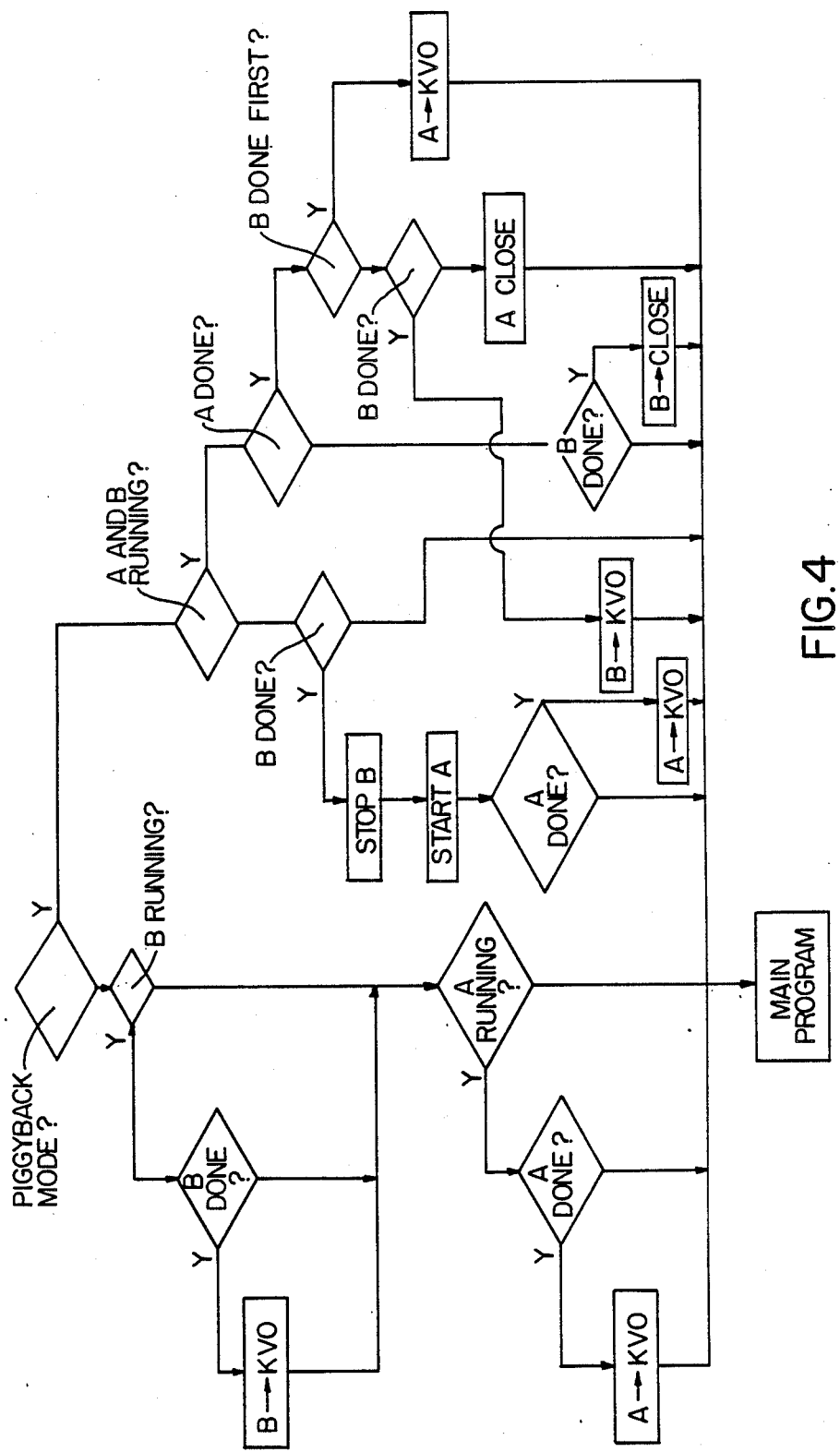
FIG. 4 is a logic diagram illustrating the operation of the system of FIG. 1 for the completion phase of operation.

It will be appreciated that the foregoing described flow sensor provides a very efficient and accurate means for detecting the occurrence of a drop in the drip chamber and for transmitting an appropriate signal to the central processing unit for providing appropriate control of a stepper motor 52. The stepper motor controls a clamp which selectively opens and closes the IV tubing to the flow of fluid thereby regulating the infusion rate of the fluid. In accordance with the invention two separate channels are provided whereby separate fluids may be administered separately, concurrently or in sequence as desired. FIG. 3 is a logic diagram illustrating the logic employed at the commencement of an infusion for integrating the two channels into a coordinated infusion system. FIG. 4 illustrates a logic diagram for the completion of the infusion. The KVO commands referenced in FIG. 4 direct the execution of a routine to maintain a low rate of fluid flow which is sufficient to keep the vein of the patient open and prevent clogging at the needle.

While a preferred embodiment of the foregoing invention has been set forth for purposes of illustration, the foregoing description should not be deemed a limitation of the invention herein. Accordingly, various modifications and adaptations and alternatives may occur to one skilled in the art without departing from the spirit and scope of the present invention.

What is claimed is:

1. A flow sensor for detecting the drop rate in an associated drip chamber of an infusion system comprising:
    infrared light emitting means to generate an infrared light path;
    sensor means interposed in said light path to detect the level of light passing therein and continuously generate a first signal indicative thereof;
    pulsing means to periodically energize said light emitting means to produce a series of energized and non-energized states;
    difference means to determine the difference between said first signal when said light emitting means is energized and said first signal when said light emitting means is not energized and generate a second signal indicative thereof;
    reference means to establish a reference level for said second signal;
    detection means to detect a pre-established deviation of a second signal from said reference level and produce a third signal indicative thereof; and
    output means to produce an output pulse in accordance with said third signal.

2. The flow sensor of claim 1 wherein the ratio between the time of energization of said light emitting means to non-energization is on the order of 1 to 9.

3. The flow sensor of claim 1 wherein the time duration of said deviation is substantially equal to the time duration of said output pulse.

4. The flow sensor of claim 1 further comprising current regulator means to maintain the periodic light level output of said light emitting means at a substantially constant level.

5. The flow sensor of claim 1 further comprising a case enclosing said sensor means and light emitting means, said case being formed of an infrared transparent material and configured so that said light path transverses spaced portions of said case.

6. A flow sensor assembly for mounting an associated drip chamber of an infusion system for detecting the drop rate in said chamber comprising:
    a case defining a central channel for receiving a drip chamber assembly, said case being formed of a material which is substantially transparent to light in the infrared region and absorbs substantially all of the light in the visible region;

infrared light emitting means mounted interiorily of said case to generate an infrared light path traversing across said channel through spaced portions of said case;

sensor means mounted interiorly of said case generally diametrally of said light emitting means in said light path to detect the level of light therein and generate a signal indicative thereof; and circuit means mounted interiorly of said case and responsive to said signal to produce an output pulse in response to a drop traversing said light path.

7. The flow sensor of claim 6 wherein said emitting means comprises an array of light emitting diodes and said sensor means comprises a photo transistor.

8. The flow sensor of claim 6 further comprising pulse menas to periodically energized said light emitting diodes to produce a sequence of energized and non-energized states.

* * * * *